(12) United States Patent
Ziegler et al.

(10) Patent No.: US 8,766,496 B2
(45) Date of Patent: Jul. 1, 2014

(54) LINEAR ELECTRIC MOTOR

(75) Inventors: Frank Ziegler, Karben (DE); Robert Schaefer, Frankfurt am Main (DE); Uwe Schober, Glashütten-Schlossborn (DE); Thomas Meinke, Kelkheim (DE)

(73) Assignee: Braun GmbH, Kronberg (DE)

( * ) Notice: Subject to any disclaimer, the term of this patent is extended or adjusted under 35 U.S.C. 154(b) by 312 days.

(21) Appl. No.: 13/190,287

(22) Filed: Jul. 25, 2011

(65) Prior Publication Data
US 2012/0019079 A1    Jan. 26, 2012

(30) Foreign Application Priority Data
Jul. 23, 2010    (EP) .................................... 10007716

(51) Int. Cl.
*H02K 33/00* (2006.01)
*H02K 33/16* (2006.01)

(52) U.S. Cl.
USPC .............. 310/29; 310/12.15; 310/17; 310/20; 310/28

(58) Field of Classification Search
USPC ................. 310/36, 37, 38, 47, 50, 25, 28–30, 310/12.15, 17, 20
See application file for complete search history.

(56) References Cited

U.S. PATENT DOCUMENTS

| | | | |
|---|---|---|---|
| 4,001,658 A * | 1/1977 | Frenk | 318/37 |
| 4,802,255 A | 2/1989 | Breuer et al. | |
| 4,831,292 A * | 5/1989 | Berry | 310/15 |
| 5,396,678 A | 3/1995 | Bredall et al. | |
| 5,836,769 A | 11/1998 | Spencer | |
| 5,980,542 A | 11/1999 | Saldivar | |
| 6,041,461 A | 3/2000 | Ogawa et al. | |
| 6,041,467 A | 3/2000 | Roberts et al. | |
| 6,058,541 A | 5/2000 | Masterman et al. | |
| 6,102,923 A | 8/2000 | Murayama | |
| 6,108,851 A | 8/2000 | Bredall et al. | |
| 6,151,745 A | 11/2000 | Roberts et al. | |
| 6,199,242 B1 | 3/2001 | Masterman et al. | |
| 6,308,367 B1 | 10/2001 | Beals et al. | |
| 6,402,768 B1 | 6/2002 | Liebel | |
| 6,453,497 B1 | 9/2002 | Chiang et al. | |
| 6,553,604 B1 | 4/2003 | Braun et al. | |
| 6,564,416 B1 | 5/2003 | Claire et al. | |
| 6,826,797 B1 | 12/2004 | Chenvainu et al. | |

(Continued)

FOREIGN PATENT DOCUMENTS

| | | |
|---|---|---|
| DE | 103 55 446 A1 | 6/2005 |
| WO | WO 2005/006538 A1 | 1/2005 |
| WO | WO 2005/062445 A1 | 7/2005 |

OTHER PUBLICATIONS

International Search Report for PCT/IB2011/053316, dated Nov. 29, 2011.

*Primary Examiner* — Burton Mullins
(74) *Attorney, Agent, or Firm* — John P. Colbert; George H. Leal

(57) ABSTRACT

A linear electric motors including a housing, a first armature movable on a first essentially linear path with respect to the housing, and a second armature movable on a second essentially linear path with respect to the housing, wherein the first armature is mounted to the housing by a first mounting spring, wherein the first armature and the second armature are coupled to each other by a coupling spring, and wherein the second armature is mounted to the housing by a second mounting spring.

14 Claims, 3 Drawing Sheets

(56) References Cited

U.S. PATENT DOCUMENTS

| | | |
|---|---|---|
| 6,873,067 B2 * | 3/2005 | Ichii et al. ............ 310/15 |
| 6,993,804 B1 | 2/2006 | Braun et al. |
| 7,143,462 B2 | 12/2006 | Hohlbein |
| 7,443,059 B2 * | 10/2008 | Kobayashi et al. ........ 310/12.04 |
| 7,594,293 B2 | 9/2009 | Xi et al. |
| 7,607,189 B2 | 10/2009 | Moskovich |
| 7,707,677 B2 | 5/2010 | Moskovich et al. |
| 7,721,376 B2 | 5/2010 | Hohlbein |
| 7,836,539 B2 | 11/2010 | Moskovich et al. |
| 7,908,699 B2 | 3/2011 | Hohlbein et al. |
| 7,931,913 B2 | 4/2011 | Mythen |
| 7,934,284 B2 | 5/2011 | Braun et al. |
| 7,941,886 B2 | 5/2011 | Chenvainu et al. |
| 7,975,344 B2 | 7/2011 | Braun et al. |
| 2002/0059685 A1 | 5/2002 | Paffrath |
| 2004/0134007 A1 | 7/2004 | Davies |
| 2004/0177462 A1 | 9/2004 | Brown et al. |
| 2004/0255416 A1 | 12/2004 | Hohlbein |
| 2005/0000043 A1 | 1/2005 | Chan et al. |
| 2005/0038461 A1 | 2/2005 | Phillips |
| 2006/0026784 A1 | 2/2006 | Moskovich |
| 2006/0175909 A1 * | 8/2006 | Kraus ............ 310/12 |
| 2007/0140959 A1 | 6/2007 | Park et al. |
| 2008/0189888 A1 | 8/2008 | Hohlbein |
| 2009/0007357 A1 | 1/2009 | Meadows et al. |

* cited by examiner

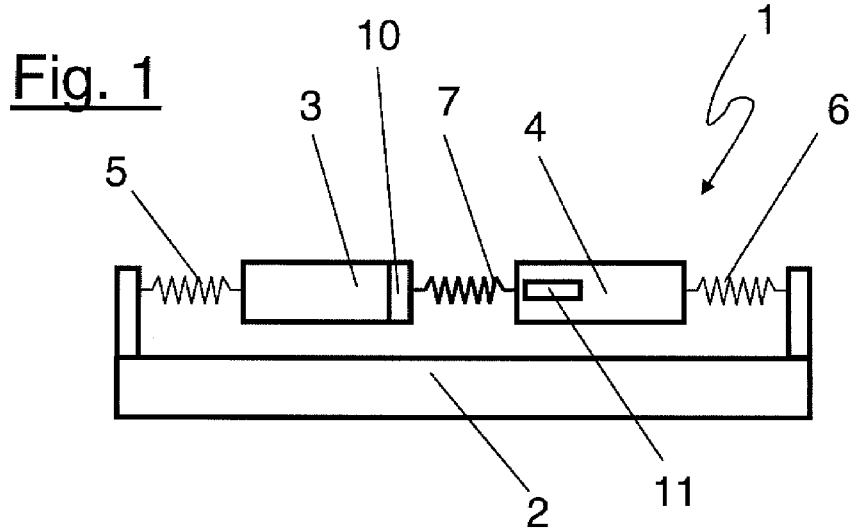
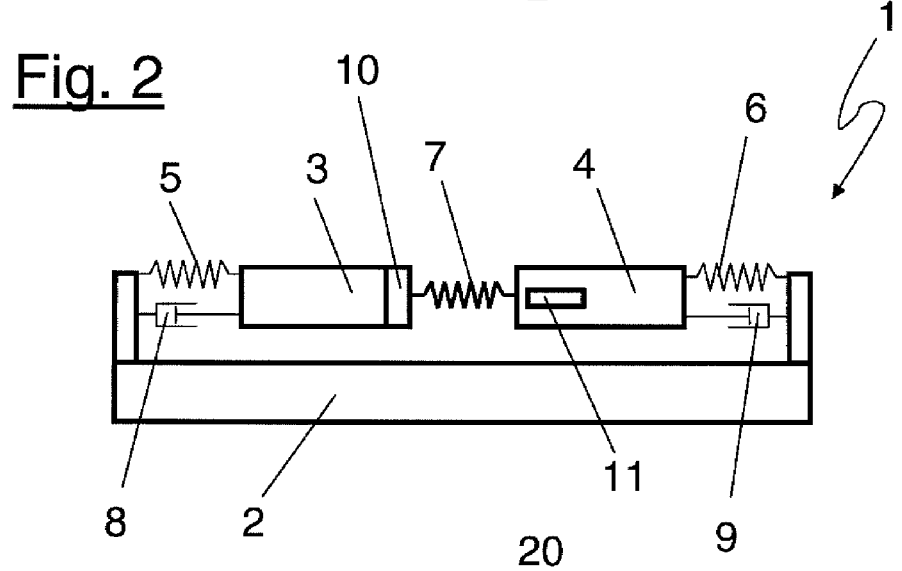
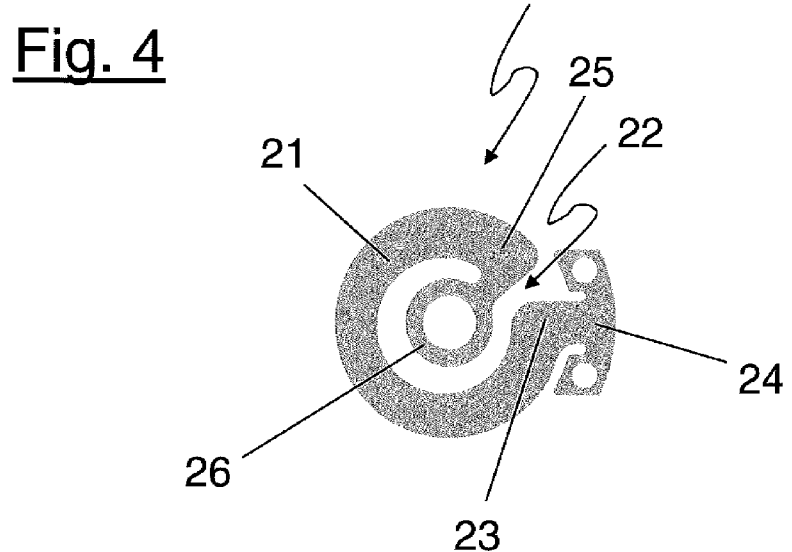

LINEAR ELECTRIC MOTOR

FIELD OF THE INVENTION

The invention relates to the field of linear electric motors and further to the field of electric household appliances comprising a linear electric motor.

BACKGROUND OF THE INVENTION

It is common in the prior art to drive electric household appliances, such as for example electric toothbrushes and shavers, by a rotating electric motor. However, it turns out that under certain conditions the noise emission by the rotating electric motor exceeds what is considered a level of comfort for a user. Accordingly there are multiple efforts in the prior art for a replacement of a rotating electric motor by a linear electric motor. However, a linear motor having an armature being movable with respect to the housing and a stator being mounted to the housing can lead to a transfer of oscillations to the housing. These transferred oscillations can strongly influence the feeling the user has when using the device.

An arrangement is known wherein the stator is not rigidly mounted to the housing. In this arrangement, the stator is elastically mounted to the housing by a spring and therefore movable with respect to the housing. The stator and the armature are coupled by a further spring such that the stator and the armature oscillate with a 180 degrees phase shift. Therefore in principle a reduction in the transfer of oscillations to the housing is achieved. However, in order to obtain a sufficient momentum transfer for the armature, the spring coupling the stator to the housing may have a fairly high spring constant. Because of the fairly high spring constant, substantial transfer of vibrations to the housing can occur. In general linear motors are discussed in WO 2005/062445 A1.

SUMMARY OF THE INVENTION

It is therefore a desire to provide a linear electric motor which under practical conditions will substantially reduce a transfer of vibrations to the housing.

In a further aspect of the invention, it is a desire to provide a linear motor having two armatures (moving parts) for driving two functional elements of an electric appliance.

In addition it may be a desire of the present invention to provide a linear electric motor which does not require any bush bearing or rolling bearing for supporting of the armature.

At least one of the above desires is satisfied by a linear electric motor comprising a housing, a first armature movable on a first essentially linear path with respect to the housing, and a second armature movable on a second essentially linear path with respect to the housing. The first armature may be mounted to the housing by a first mounting spring. For example, the first armature may be mechanically attached with respect to the housing solely by the first mounting spring, i.e. no further bearings are provided. Also, the first armature and the second armature may be coupled to each other by a coupling spring. The first armature, the second armature or the housing may comprise a coil (for example, a solenoid). The second armature may be mounted to the housing by a second mounting spring (for example, the second armature may be mechanically held with respect to the housing solely by the second mounting spring, i.e. no further bearings are provided). The linear electric motor as proposed may be an oscillating linear electric motor, where the first and second armatures move in an oscillating linear manner along their respective essentially linear paths. The linear paths are insofar essentially linear as the armatures may deviate from a perfect linear path by 10 or less micrometers per millimeter moved in the linear direction. Here, "essentially linear" means that the deviation from a perfect linear path is 1% or less.

In an embodiment of the proposed linear electric motor, the first armature as well as the second armature is each mounted via respective mounting springs to the housing, which leads to a decoupling, in part, of the housing from vibrations induced in operation via the motion of the first and second armatures. This decoupling works in particular for embodiments of the invention, wherein the first armature, the second armature, the first mounting spring, the second mounting spring and the coupling spring are arranged such that the first armature and the second armature move with a phase shift of 180 degrees when in operation. Because of the phase shift of 180 degrees between the first armature and the second armature, the vibrations transferred to the housing may cancel each other out to at least some extent if not completely. For example, vibrations transferred to the housing via the first armature can be cancelled, at least in part, by vibrations transferred to the housing via the second armature.

In an embodiment, one of the first and second armatures comprises a coil (i.e. the coil may be mounted to the respective armature), which is interacting with the other one of the first and second armatures inducing an attractive or repulsive force between the two armatures. The other one of the first and second armatures may comprise at least one permanent magnet for interaction with the coil. Due to the magnetic forces applied between the two armatures they can move in opposite directions, i.e. 180 degrees out of phase, independent from the specific realizations of the first and second mounting springs or the coupling spring.

In an embodiment, the coil may be attached to the housing interacting with at least one of the first and second armatures. In an embodiment the coil is attached to the housing and interacts with one of the first and second armatures while the other armature is driven via the coupling provided by the coupling spring. In an embodiment of the linear electric motor, the armature interacting with the coil attached to the housing comprises a permanent magnet.

In order to provide an oscillating motion the current flow through the coil may be controlled such that it is intermittent. The current flow may be interrupted when the two armatures reach their maximum amplitude of the oscillating linear motion. The coupling spring as well as the two mounting springs can then force the two armatures back to their respective rest positions.

In an embodiment, the ratio between a spring constant of the first mounting spring in a direction parallel to the linear path of the first armature and a spring constant of the second mounting spring in a direction parallel to the linear path of the second armature equals the ratio between a mass of the first armature and a mass of the second armature in order to optimize the decoupling of the oscillating masses of the armatures from the housing.

In an embodiment, the linear paths of the first armature and the second armature are parallel to each other or even partly identical. Although a compensation of the oscillating armatures can also be achieved when the paths of the armatures are neither parallel to each other nor identical with each other, parallel or partly identical paths enhance the compensation.

In a further embodiment, the second armature comprises an elongated body with a channel being parallel to the second linear path and wherein the first armature comprises an elongated body extending in a direction parallel to the first linear path through the channel of the second armature. This way the two armatures move on paths being essentially identical. This particular arrangement further reduces the footprint of the linear motor having two armatures.

In an embodiment a first side of the first armature is mounted to the housing by the first mounting spring, and a second side of the second armature is mounted to the housing by the second mounting spring, wherein the second side of the second armature is located opposite the first side of the first armature. In this configuration, the two mounting springs can act in opposite directions onto the two armatures moving out of phase thus compensating the restoring forces acting from the two mounting springs onto the housing. Due to the configuration, the forces acting on the housing can cancel each other out or at least a portion thereof. This minimizes the amount of vibration felt by the user while gripping the housing.

Further the location of the two mounting springs at opposite sides of the coupled first and second armatures does provide the required mechanical stability of the mounting of the two armatures. In an embodiment, the first and second armatures can be operated without any further bearing in addition to the first and second mounting springs.

The mechanical stability can be enhanced if the linear electric motor comprises two coupling springs between the first armature and the second armature wherein the first coupling spring is located between a first side of the first armature and a first side of the second armature and the second coupling spring is located between a second side of the first armature and second side of the second armature.

A mechanical design of the linear electric motor without any additional bearings is enabled by providing a mechanical coupling between the first and the second armatures by a coupling spring and mounting the first armature by a first mounting spring to the housing and mounting the second armature by a second mounting spring to the housing. Therefore in an embodiment, the first mounting spring comprises a first spring constant in a direction parallel to the first linear path that is smaller than a second spring constant in at least one direction being perpendicular to the first linear path, and the second mounting spring comprises a first spring constant in a direction parallel to the second linear path that is smaller than a second spring constant in at least one direction being perpendicular to the second linear path.

In an embodiment, the first mounting spring may comprise a spring constant in at least one direction being perpendicular to the first linear path which is by at least a factor of 5, a factor of 10, a factor of 20, a factor of 50 or a factor of 100 larger than a spring constant of the first mounting spring in a direction parallel to the first linear path.

In a further embodiment, the second mounting spring may comprise a spring constant in at least one direction being perpendicular to the second linear path which is by at least a factor of 5, a factor of 10, a factor of 20, a factor of 50 or a factor of 100 larger than a spring constant of the second mounting spring in a direction parallel to the second linear path.

In a further embodiment, the coupling spring comprises a spring constant in a direction parallel to the first linear path and/or the second linear path being smaller than a spring constant in at least one direction being perpendicular to the first linear path and/or to the second linear path.

In an embodiment, the coupling spring comprises a spring constant in at least one direction being perpendicular to the first and/or second linear path which is by at least a factor of 5, a factor of 10, a factor of 20, a factor of 50 or a factor of 100 larger than a spring constant of the coupling spring in a direction parallel to the first and/or second linear path.

This way either the first mounting spring, the second mounting spring or the coupling spring or all of them do function as a spring in a direction parallel to the linear paths of the first and second armatures while providing a more or less rigid support in at least one direction being perpendicular to the direction of the path.

In a further embodiment, the spring constants of the coupling spring and/or the mounting spring in a direction parallel to the linear path is smaller than spring constants in two directions being perpendicular to the linear path and being perpendicular to each other.

In an embodiment, such a spring is provided by a leaf spring which is optionally formed by a ring segment, in particular a ring being interrupted at one section such that it effectively forms a spring.

In an embodiment, the leaf spring comprises a first mounting section extending radially outwardly from one end of the ring segment and a second mounting section extending radially inwardly from a second end of the ring segment. Once such a leaf spring is used as a mounting spring it may be advisable that the first mounting section is mounted to the housing while the second mounting section is mounted either to the first or to the second armature. Once such a leaf spring is used as a coupling spring one of the armatures may be mounted to the first mounting section while the second armature may be mounted to the second mounting section.

In an embodiment, the first armature comprises a damper having a damping constant and the second armature comprises a damper having a damping constant while the damping of the first armature and the damping of the second armature are chosen such that the forces provided by the movements of the first armature and the second armature equal each other. The force F provided by each of the armatures when in motion can be calculated as F=k multiplied by v, wherein k is the damping constant and v is the velocity of the respective armature. Damping of the first and the second armatures may be introduced by sealings provided between the first armature or the second armature and the housing. The sealings can also reduce the likelihood of moisture entering into the housing.

At least one of the above desires is further satisfied by an electric household appliance comprising an electric linear motor as described before.

In a particular embodiment of the electric household appliance a first armature is coupled to a first functional element of the household appliance and a second armature is coupled to a second functional element of the household appliance.

Examples for household appliances in the sense of the present application are electric toothbrushes and electric shavers.

BRIEF DESCRIPTION OF THE DRAWINGS

The proposed linear electric motor will be further elucidated by detailed explanation of exemplary embodiments and by reference to figures. In the figures FIG. 1 shows a schematic mechanical representation of the linear electric motor according to an embodiment of the invention, FIG. 2 shows a schematic representation of an embodiment of a linear electric motor including damping, FIG. 4 shows a schematic side view of a spring as used in one of the embodiments according to FIGS. 1 to 3.

DETAILED DESCRIPTION OF THE INVENTION

Figure 3:
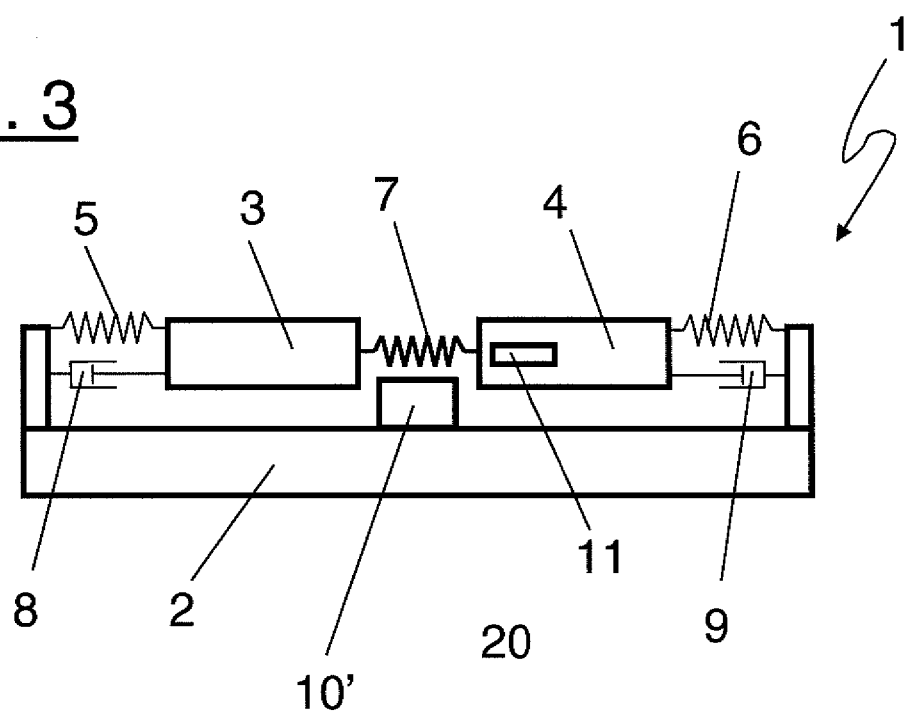
FIG. 3 shows a schematic representation of an alternative embodiment of a linear electric motor.

As used herein, the term "armature" means a moving part of an electromagnetic device.

FIG. 1 depicts a schematic representation of the linear electric motor according to an exemplary embodiment. The electric motor 1 comprises a housing 2, a first armature 3 and a second armature 4. The first armature 3 is mounted to the housing 2 by a first mounting spring 5 whereas the second armature 4 is mounted to the housing 2 by a second mounting spring 6. The first and the second armatures 3, 4 are coupled to each other by a coupling spring 7.

In the embodiment shown in FIG. 1, the first armature 3 comprises a coil 10 and the second armature 4 comprises a permanent magnet 11.

The magnetic forces applied between the first and second armatures 3, 4 can cause the first armature 3 and the second armature 4 to move in opposite directions, i.e. 180 degrees out of phase (in the ideal case, where no additional damping of the oscillating masses of the first and second armature is present). Further the spring constant of the coupling spring 7 can be chosen such that its resonance frequency corresponds to the oscillation frequency of the first and second armature 3, 4 which is imposed by the coil 10 and the permanent magnet 11. The coupling spring 7 on its own can force the first and second armatures 3, 4 to move with a phase shift of 180 degrees when in motion. The coupling spring supports the 180 degrees phase shift motion of the first and second armature 3, 4.

In order to provide an oscillating motion the current flow through the coil 10 can be controlled such that it is intermittent. The current flow can be interrupted when the first and second armature 3, 4 reach the maximum amplitude of the oscillating motion. The coupling spring 7 as well as the two mounting springs 5, 6 can then force the first and second armature 3, 4 back to their respective starting positions.

As the first and second mounting springs 5, 6 are attached to the two armatures at opposing sides thereof they provide counter acting forces on the housing 2. Due to the first and second armature 3, 4 being out of phase, in a first cycle of motion the first mounting spring 5 pushes or presses on the housing while the second mounting spring 6 pulls on the housing 2. As these forces are in opposite directions, the two restoring forces act on the housing 2 in opposite directions cancelling each other. In a second cycle of motion, the first mounting spring 5 pulls on the housing 2 while the second mounting spring 2 pushes or presses on the housing 2. Again, the forces applied to the housing 2 via the springs 5, 6 act in opposite directions such that the restoring forces of the housing 2 also act in opposite directions and thereby cancel each other out at least partially if not completely. Thus the amount of vibrational oscillations transferred from the first and second armature 3, 4 to the housing 2 can be reduced or precluded altogether.

To achieve this, the spring constants are chosen such that $$\frac{D_1}{D_2} = \frac{m_1}{m_2},$$

wherein $D_1$ is the spring constant of the first mounting spring 5, $D_2$ is the spring constant of the second mounting spring 6, $m_1$ is the mass of the first armature 3 and $m_2$ is the mass of the second armature 4.

In order to avoid deviations from a phase shift of 180 degrees between the first armature 3 and the second armature 4, any damping of the oscillation performed by the first armature 3 and the second armature 4 should be carefully balanced. For example, a situation where the oscillation is influenced by a damping is in principle depicted in FIG. 2. The first armature 3 comprises a first damper 8 and the second armature 4 comprises the second damper 9. Those dampers 8, 9 may be formed by sealings, for example in the form of elastomeric plastic material sections, which couple to the first and second armatures 3,4, respectively, and serve to avoid any penetration of liquids into the housing 2.

In FIG. 2 elements being identical to the elements depicted also in the embodiment according to FIG. 1 are denoted by the same reference numbers.

The damping constants k of the first damper 8 and the second damper 9 have to be chosen such that the forces provided by the first armature 3 and the second armature 4 when in motion equal each other. In a situation when the first armature and the second armature do move with a 180 degrees phase shift, i.e. in opposite directions, this will lead to a cancellation of forces transferred to the housing from the first and second armatures 3, 4.

In order to provide a functionality not only as springs but also as elements giving mechanical stability in any direction perpendicular to the paths of motion of the first armature 3 and the second armature 4 each of the springs 5, 6, 7 may be designed as shown in FIG. 4.

The leaf spring 20 shown in FIG. 4 would be mounted in the arrangements shown in FIGS. 1 and 2 such that the ring segment 21 would be perpendicular to the plane of the paper on which FIGS. 1 and 2 are drawn. The ring segment 21 having an interruption 22 provides the required flexibility in a direction perpendicular to the paper of FIG. 4. In all directions parallel to the plane of the paper of FIG. 4 the ring segment 21 has an extension such that in a radial direction of the ring 21 the ring provides a more or less rigid support.

In particular the spring constant of the spring 20 in a direction perpendicular to the plane of the paper in FIG. 4 is less than any spring constant of the spring 20 in any radial direction of the spring in the plane of the paper. At its first end 23 the ring 21 comprises a first mounting section 24 extending radially outwardly from the ring 21. At its second end 25 the ring 21 comprises a second mounting section 26 extending radially inwardly from the ring 25. It will be apparent from the description of the practical embodiment as depicted in FIG. 3 how the housing and the two armatures are mounted to a spring as shown in FIG. 4.

Although the leaf spring 20 is shown having a circular contour/arrangement. Any other suitable shape may be utilized. For example, leaf springs of the present invention may comprise a triangular outer periphery, a square periphery, a rectangular periphery, a polygonal periphery, or any other suitable shape. The leaf spring 20 should provide a low spring constant in a direction parallel to the linear motion of the first and/or second armature 3, 4 and a higher spring constant in a direction perpendicular to the linear motion of the first and/or second armature 3, 4.

An alternative embodiment of the linear electric motor according to the present invention is schematically shown in FIG. 3. The embodiment depicted in FIG. 3 differs from the embodiments according to FIGS. 1 and 2 by the coil 10' being attached to the housing 2 and not to one of the armatures 3, 4 as in FIGS. 1 and 2. In such embodiments, the coil 10' may interact only with the permanent magnet 11 of the second armature 4. The first armature in turn can be driven by the coupling between the first armature 3 and the second armature 4 provided by the coupling spring 7. Thus no wiring of any movable parts is required.

Figure 5:
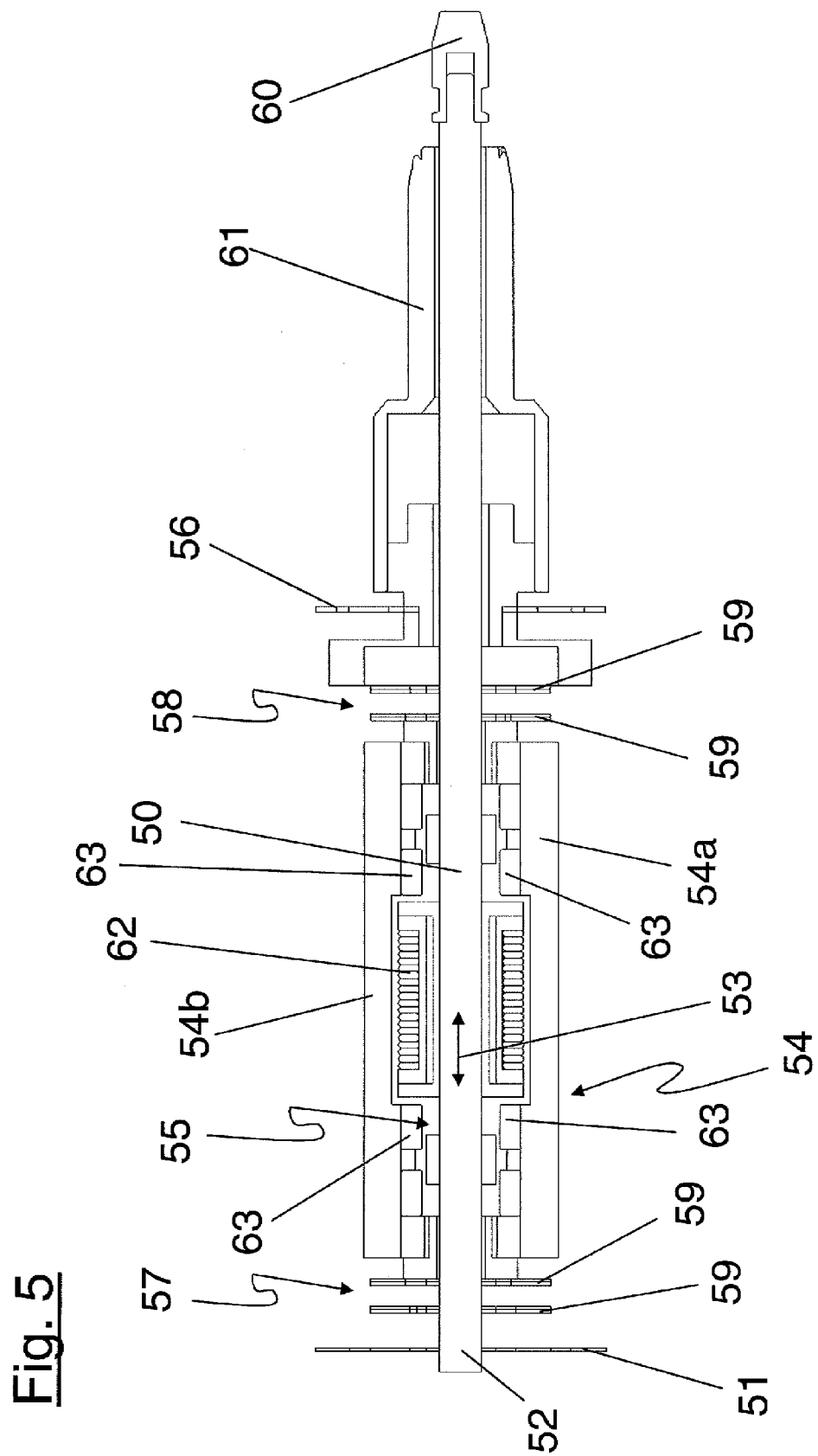
FIG. 5 shows a cross-sectional view of a linear electric motor according to an embodiment of the present invention.

FIG. 5 shows a further exemplary embodiment of a linear electric motor. The embodiment shown in FIG. 5 corresponds to what has been schematically described with reference to FIG. 3. All parts which are shown in the schematic representation of FIG. 3 can be found in the embodiment according to FIG. 5. The first armature 50 of the embodiment of FIG. 5 has the form of a rod or axis 50.

The first armature 50 is mounted to the housing 2 by a mounting spring 51. The mounting spring 51 can be attached to the first armature 50 adjacent a first end 52 of the armature 50. When viewed from the side the first mounting spring 51 has a design as depicted in principle in FIG. 4 allowing the first armature 50 to perform an oscillating motion in a direction 53. Due to its design, the mounting spring 51, in a direction perpendicular to the direction 53 of motion of the first armature 50, provides a stable support of the first armature 50.

The second armature 54 comprises two parts 54a, 54b on each side of the first armature 50. The two parts 54a and 54b are attached to each other, such that they move as a single part.

The second armature 54 forms a channel 55 between its two halves 54a and 54b. The first armature 50 extends through this channel 55 of the halves 54a and 54b of the second armature 54. The first and second armatures 50, 54 experience an oscillating motion along the same path 53 during operation. The second armature 54 is mounted via a second mounting spring 56 to the housing 2. While the housing 2 is attached to the first mounting sections (denoted as 24 in FIG. 4) of the two mounting springs (51, 56) the first armature 50 and the second armature 54, respectively are mounted to the second mounting sections (denoted as 26 in FIG. 4) of the mounting springs 51, 56.

The second mounting spring 56 is attached adjacent a second end 75 or side of the second armature 54 which is opposite to the first end 52 of the first armature 50. When the first and second armatures 50, 54 move 180 degrees out of phase, the retraction forces transferred from each of the two mounting springs 51, 56 onto the housing should compensate each other. Namely, the forces transferred to the housing 2 should cancel each other out or at least a portion thereof such that vibrations felt by the user gripping the housing 2 are greatly reduced and/or precluded.

The first and second armatures 50, 54 may be coupled to each other via two coupling springs 57, 58. Each of the two coupling springs 57, 58 may comprise two leaf springs 59 which in principle have a design as depicted schematically in FIG. 4. A combination of two springs 59 for each of the two coupling springs 57, 58 may be chosen to be able to easily vary the spring constant of the composed springs 57, 58. The first armature 50 is mounted to the second mounting section (denoted as 26 in FIG. 4) while the second armature 54 is mounted to the first mounting section (denoted as 24 in FIG. 4) of the springs 59.

As described before for the embodiment according to FIG. 3, a coil 62 can be attached to the housing 2 providing an interaction with the second armature 54. The second armature 54 may further comprise a set of four permanent magnets 63 in order to allow a magnetic and/or electrical coupling between the second armature 54 and the coil 62 at the housing 2. Embodiments are contemplated where greater than four permanent magnets are utilized. Embodiments are also contemplated where less than four permanent magnets are utilized.

The spring constants of the coupling springs 57, 58 are chosen such that their resonance frequency corresponds to the oscillation frequency which is imposed by the electric drive consisting of the coil 62 and the magnets 63.

In order to provide an oscillating motion, the current flow through the coil 62 can be controlled such that it is intermittent. The current flow can be interrupted when the first and second armatures 50, 54 reach the maximum amplitude of their oscillating motion. The coupling springs 57, 58 as well as the two mounting springs 52, 56 then can force the two armatures 50, 54 back to their respective starting positions.

Each of the first and second armature 50, 54 comprises connectors 60, 61 for coupling the linear electric motor to functional elements of a household appliance.

In embodiments where the household appliance comprises a toothbrush, the toothbrush may comprise a plurality of contact elements on a head of the device. The contact elements may comprise any suitable material and/or configuration. Additionally, it should be noted that the contact elements may comprise any suitable contact element and/or may comprise elements which are utilized for massaging gums, cleaning the tongue, providing chemistry to an area of the oral cavity, e.g. antimicrobial agents, malodor agents, flavor agents, anti-plaque agents, anti-gingivitis agents, whitening agents, or the like.

For example, in some embodiments, the contact elements may comprise tufts. The tufts may comprise a plurality of individual filaments which are securely attached to the head. Such filaments may be polymeric and may include, for example, polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 mm to about 15 mm, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, tapered tip, a pointed tip. In some embodiments, the filaments may include a dye which indicates wear of the filaments as described in U.S. Pat. No. 4,802,255. Some examples of suitable filaments for use with the brush of the present invention are described in U.S. Pat. No. 6,199,242. Other suitable examples of bristles include textured bristles, e.g., single and multicomponent bristles (e.g., bristles formed by coextruding different polymers), crimped bristles, gum massaging bristles, bristles of varying configurations (e.g., bristles having multiple lumens), and/or combinations thereof. Other suitable examples of contact elements include those described in U.S. Patent Application Publication Numbers 2002/0059685; 2005/0000043; 2004/0177462; 2005/0060822; 2004/0154112; U.S. Pat. Nos. 6,151,745; 6,058,541; 6,041,467; 6,553,604; 6,564,416; 6,826,797; 6,993,804; 6,453,497; 6,993,804; 6,041,467; and U.S. patent application Ser. No. 12/008,073, filed on Jan. 8, 2008, entitled, "TOOTHBRUSHES" and Ser. No. 60/928,012, filed on May 7, 2007, entitled "ORAL HYGIENE IMPLEMENTS", all of which are herein incorporated by reference in their entirety. Additionally, any suitable arrangement of contact elements may be utilized. Some suitable examples include those described in U.S. Pat. Nos. 5,836,769; 6,564,416; 6,308,367; 6,108,851; 6,058,541; and 5,396,678.

In addition to bristles and/or bristle tufts, the contact elements may also include elastomeric structures, foams, combinations thereof, and the like. For example, the contact elements may comprise elastomeric fins as described in U.S. Pat. No. 6,553,604 and U.S. Patent Application Publication No.

2007/0251040A1. As yet another example, the contact elements may comprise elastomeric cup shaped elements as described in U.S. Patent Publication No. 2004/0154112A1. In some embodiments, the contact elements may comprise a combination of elastomeric elements and bristles. As an example, a combination of fins and bristles may be utilized, a combination of an elastomeric cup(s) and bristles may be utilized, and/or combinations of elastomeric elements either alone or in combination with bristles may be utilized. Combinations of elastomeric contact elements are described in U.S. Patent Publication No. 2009/0007357A1.

The contact elements and/or massaging elements may be attached to the head in any suitable manner. Conventional methods include stapling, anchor free tufting, and injection mold tufting. For those contact elements that comprise an elastomer, these elements may be formed integral with one another, e.g. having an integral base portion and extending outward therefrom or discretely. The elastomer elements may be injection molded in the head.

In addition to the contact elements described heretofore, the head may comprise a soft tissue cleanser constructed of any suitable material. Some examples of suitable material include elastomeric materials; polypropylene, polyethylene, etc; the like, and/or combinations thereof. The soft tissue cleanser may comprise any suitable soft tissue cleansing elements. Some examples of such elements as well as configurations of soft tissues cleansers on a toothbrush are described in U.S. Patent Application Nos. 2006/0010628; 2005/0166344; 2005/0210612; 2006/0195995; 2008/0189888; 2006/0052806; 2004/0255416; 2005/0000049; 2005/0038461; 2004/0134007; 2006/0026784; 20070049956; 2008/0244849; 2005/0000043; 2007/140959; and U.S. Pat. Nos. 5,980,542; 6,402,768; and 6,102,923.

Additionally, for those embodiments comprise elastomer elements on a first side of the head and a second side of the head, the second side being opposite the first side, the elastomer elements of both sides of the head may be unitarily formed. For example, the head sans the elastomeric elements may comprise openings therethrough which can allow elastomeric material to flow from the first side of the head to the second side of the head.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCE LISTING

1 Electric motor
2 Housing
3 First armature
4 Second armature
5 First mounting spring
6 Second mounting spring
7 Coupling spring
8 First damper
9 Second damper
10, 10' Coil
11 Permanent magnet
20 Leaf spring
21 Ring segment
22 Gap
23 First end
24 First mounting section
25 Second end
26 Second mounting section
50 First armature
51 First mounting spring
52 First end of the first armature 50
53 Path of motion
54, 54a, 54b Second armature
55 Channel
56 Second mounting spring
57, 58 Coupling springs
59 Leaf springs
60, 61 Connectors
62 Coil
63 Permanent magnets

The invention claimed is:

1. Linear electric motor comprising:
a housing (2); and
a first armature movable on a first essentially linear path with respect to the housing, and a second armature movable on second essentially linear path with respect to the housing, the first armature mounted to the housing by a first mounting spring, the first armature and the second armature coupled to each other by a coupling spring, wherein the second armature is mounted to the housing by a second mounting spring; and a coil comprising by the first armature, the second armature or the housing, wherein the first armature and the second armature are in electromagnetic communication with the coil, and wherein the first mounting spring and the second mounting spring are configured to transmit opposite forces to the housing such that the opposite forces cancel at least a portion of each other out;
wherein one of the first and second armatures includes at least a permanent magnet; and
wherein the first mounting spring and the second mounting spring function as a spring in a direction parallel to the linear paths of the first and second armatures while providing a rigid support in at least one direction perpendicular to the direction of the path; and
wherein the first mounting spring includes a spring constant in a direction parallel to the first essentially linear path smaller by at least a factor of 10 than a spring constant in at least one direction perpendicular to the first essentially linear path, and wherein the second mounting spring includes a spring constant in a direction parallel to the second essentially linear path smaller by at least a factor of 10 than a spring constant in at least one direction perpendicular to the second essentially linear path.

2. Linear electric motor according to claim 1, wherein the first armature, the second armature, the first mounting spring, the second mounting spring and the coupling spring are arranged such that the first armature and the second armature move with a phase shift of essentially 180° when in operation.

3. Linear electric motor according to claim 1, wherein a ratio between the spring constant of the first mounting spring in a direction parallel to the essentially linear path of the first armature and a spring constant of the second mounting spring in a direction parallel to the essentially linear path of the second armature equals the ratio between a mass of the first armature and a mass of the second armature.

4. Linear electric motor according to claim 1, wherein the essentially linear paths of the first armature and the second armature are parallel to each other.

5. Linear electric motor according to claim 4, wherein the second armature comprises an elongated body with a channel being parallel to the first linear path and to the second linear path, and wherein the first armature comprises an elongated body extending in a direction parallel to the first essentially linear path through the channel of the second armature.

6. Linear electric motor according to claim 1, wherein a first side of the first armature is mounted to the housing by the first mounting spring, and wherein a second side of the second armature is mounted to the housing by the second mounting spring, wherein the second side of the second armature is located opposite the first end of the first armature.

7. Linear electric motor according to claim 5, wherein the first armature and the second armature are coupled to each other by two coupling springs, the first coupling spring being located between a first side of the first armature and a first side of the second armature and the second coupling spring being located between a second side of the first armature and a second side of the second armature.

8. Linear electric motor according to claim 1, wherein the coupling spring comprises a spring constant in a direction parallel to the first essentially linear path and/or the second essentially linear path being smaller than a spring constant in at least one direction being perpendicular to the first essentially linear path and/or second essentially linear path.

9. Linear electric motor according to claim 1, wherein the mounting spring and/or the coupling spring is a leaf spring.

10. Linear electric motor according to claim 9, wherein the leaf spring is formed by a ring segment.

11. Linear electric motor according to claim 10, wherein the leaf spring comprises a first mounting section being arranged radially outwardly from the ring segment and a second mounting section being arranged radially inwardly from the ring segment.

12. Linear electric motor according to claim 1, wherein the first armature comprises a damper and the second armature comprises a damper, wherein the dampers are chosen such that the forces provided by the first armature and the second armature equal each other during operation.

13. Electrical household appliance comprising a linear electric motor according to claim 1.

14. Electrical household appliance according to claim 13, wherein the first armature is coupled to a first functional element and wherein the second armature is coupled to a second functional element.

* * * * *